United States Patent
Elsoee et al.

(10) Patent No.: US 9,625,376 B2
(45) Date of Patent: Apr. 18, 2017

(54) SYSTEM FOR AND METHOD OF COMBINED LIBS AND IR ABSORPTION SPECTROSCOPY INVESTIGATIONS

(71) Applicant: Foss Analytical A/S, Hilleroed (DK)

(72) Inventors: Maja Kirstine Elsoee, Birkeroed (DK); Henrik Vilstrup Juhl, Roskilde (DK); Thomas Nikolajsen, Slangerup (DK)

(73) Assignee: FOSS ANALYTICAL A/S, Hilleroed (DK)

( * ) Notice: Subject to any disclaimer, the term of this patent is extended or adjusted under 35 U.S.C. 154(b) by 0 days.

(21) Appl. No.: 14/772,555

(22) PCT Filed: Mar. 22, 2013

(86) PCT No.: PCT/EP2013/056091
§ 371 (c)(1),
(2) Date: Sep. 3, 2015

(87) PCT Pub. No.: WO2014/146719
PCT Pub. Date: Sep. 25, 2014

(65) Prior Publication Data
US 2016/0018325 A1      Jan. 21, 2016

(51) Int. Cl.
*G01J 5/00*   (2006.01)
*G01N 21/3563*   (2014.01)
(Continued)

(52) U.S. Cl.
CPC ............ *G01N 21/3563* (2013.01); *G01J 3/28* (2013.01); *G01J 3/443* (2013.01); *G01N 21/35* (2013.01);
(Continued)

(58) Field of Classification Search
CPC .... G01N 21/718; G01N 21/65; G01N 21/359; G01N 21/3563; G01N 2201/08;
(Continued)

(56) References Cited

U.S. PATENT DOCUMENTS 6,801,595 B2   10/2004   Grodzins et al.
7,999,928 B2   8/2011   Beckstead et al.
(Continued)

OTHER PUBLICATIONS

Burakov, V.S. et al. "Development of a Laser-Induced Breakdown Spectroscopy Method for Soil and Ecological Analysis (Review)." *Journal of Applied Spectroscopy* 77.5 (2010): 595-608.
(Continued)

*Primary Examiner* — Mark R Gaworecki
*Assistant Examiner* — Taeho Jo
(74) *Attorney, Agent, or Firm* — Harness, Dickey & Pierce, PLC

(57) ABSTRACT

A system (102) for determining properties of a sample (114) comprises a LIBS detector (104,106) and an infra-red absorption detector (108,110) for interrogating a sample (114) to generate LIBS spectral data and infra-red absorption spectral data respectively; and a data processor (112) adapted to apply at least one chemometric prediction model, each constructed to link, preferably quantitatively link, features of both LIBS and absorption spectral data to a different specific property of the sample, to a combined dataset derived from at least portions of both the LIBS and the absorption data to generate therefrom a determination, preferably a quantitative determination, of the specific property linked by that model.

12 Claims, 5 Drawing Sheets

(51) Int. Cl.
    *G01J 3/443*     (2006.01)
    *G01N 33/24*     (2006.01)
    *G01N 21/35*     (2014.01)
    *G01N 21/71*     (2006.01)
    *G01J 3/28*     (2006.01)
    G01N 1/28     (2006.01)
    G01J 1/08     (2006.01)

(52) U.S. Cl.
    CPC ........... *G01N 21/718* (2013.01); *G01N 33/24* (2013.01); *G01J 2001/083* (2013.01); *G01N 1/286* (2013.01); *G01N 2201/129* (2013.01)

(58) Field of Classification Search
    CPC ........... G01N 21/35; G01N 2201/0612; G01N 2201/0846; G01N 1/286; G01N 2201/129; G01N 33/24; G01J 3/443; G01J 3/28; G01J 2001/083
    USPC ...................................................... 250/338.1
    See application file for complete search history.

(56) References Cited

U.S. PATENT DOCUMENTS

| | | | | |
|---|---|---|---|---|
| 8,018,647 | B2* | 9/2011 | Rice | G01J 3/32 |
| | | | | 250/330 |
| 8,158,957 | B2* | 4/2012 | Nelson | G01J 3/2803 |
| | | | | 250/458.1 |
| 8,199,321 | B2* | 6/2012 | Yoo | B23K 26/03 |
| | | | | 356/318 |
| 9,285,272 | B2* | 3/2016 | Sackett | G01J 3/0227 |
| 2005/0200843 | A1* | 9/2005 | Kumar | A61B 5/0075 |
| | | | | 356/318 |
| 2007/0265783 | A1 | 11/2007 | Mound | |
| 2008/0198365 | A1* | 8/2008 | Treado | G01J 3/02 |
| | | | | 356/73 |
| 2009/0128802 | A1 | 5/2009 | Treado et al. | |
| 2009/0163369 | A1* | 6/2009 | Treado | G06F 19/28 |
| | | | | 506/8 |
| 2010/0085567 | A1* | 4/2010 | Dottery | G01J 3/443 |
| | | | | 356/301 |
| 2011/0080577 | A1* | 4/2011 | Nelson | G01J 3/02 |
| | | | | 356/73 |
| 2011/0237446 | A1* | 9/2011 | Treado | G06K 9/00147 |
| | | | | 506/8 |
| 2012/0038908 | A1* | 2/2012 | Beckstead | G01J 3/02 |
| | | | | 356/72 |
| 2012/0062874 | A1* | 3/2012 | Beckstead | G01J 3/02 |
| | | | | 356/72 |
| 2012/0120393 | A1 | 5/2012 | Treado et al. | |
| 2013/0242301 | A1* | 9/2013 | Berg | G01N 15/1434 |
| | | | | 356/336 |
| 2013/0320216 | A1* | 12/2013 | Aiko | G01B 11/303 |
| | | | | 250/349 |
| 2014/0022531 | A1* | 1/2014 | Sackett | G01J 3/0227 |
| | | | | 356/51 |
| 2014/0022532 | A1* | 1/2014 | Sackett | G01J 3/0227 |
| | | | | 356/51 |

OTHER PUBLICATIONS

Sattmann, R. et al. "Laser-Induced Breakdown Spectroscopy for Polymer Identification." *Applied Spectroscopy* 52.3 (1998): 456-461.

Stenberg, Bo et al. "Chapter Five: Visible and Near Infrared Spectroscopy in Soil Science." *Advances in Agronomy* 107 (2010): 163-215.

International Search Report PCT/ISA/210 for International Application No. PCT/EP2013/056091 dated Nov. 18, 2013.

* cited by examiner

SYSTEM FOR AND METHOD OF COMBINED LIBS AND IR ABSORPTION SPECTROSCOPY INVESTIGATIONS

CROSS-REFERENCE TO RELATED APPLICATIONS

This application is a national phase under 35 U.S.C. §371 of PCT International Application No. PCT/EP2013/056091 which has an International filing date of Mar. 22, 2013, the entire contents of each of which are hereby incorporated herein by reference.

The present invention relates to determining properties of a sample by utilizing laser induced breakdown spectroscopy (LIBS) in combination with infrared (IR) absorption spectroscopy.

LIBS is a well known technique which is capable of providing an elemental 'fingerprint' of a sample with high sensitivity. Its use in the analysis of soil is also well known and has been reported in, for example 'Development of a Laser-Induced Breakdown Spectroscopy Method for Soil Analysis (Review)', V. S. Burakov et al., Journal Applied Spectroscopy, Vol. 77, No. 5, 2010, Pages 595-608.

LIBS operates by focusing a laser onto a small area at the surface of the sample material to thereby ablate a very small amount of material and generate a plasma plume. The ablated material of the plasma plume breaks down into excited ionic and atomic species. The characteristic atomic emission lines of the elements can be observed in the electromagnetic spectrum of the plasma plume which is typically recorded using a spectrometer and analysed in a data processor to provide information regarding the relative amounts of chemical species present in the sample as a measure of the properties of the sample.

It is known to combine LIBS with other optical energy measurement techniques in order to provide an improved compositional determination. The combination of X-ray fluorescence measurements with LIBS, for example, is disclosed in U.S. Pat. No. 6,801,595 of Grodzins et al. LIBS is typically employed to gain information on the relatively lighter elements and typically provides data concerning the relative concentrations of elements in a sample matrix whereas X-ray fluorescence provides information on the relatively heavier elements and provides absolute concentration information. According to U.S. Pat. No. 6,801,595 spectra from the two techniques are combined and information from the two techniques regarding the same element is employed to produce an output indicative of absolute concentrations of elements in the sample matrix from the combination of both the LIBS and the X-ray fluorescence data.

A combination of Raman scattering and LIBS emission detection is disclosed by Beckstead et al. in U.S. Pat. No. 7,999,928. Raman spectroscopy is based on the scattering of light by vibrating molecules and the spectral shift (anti-Stokes or Stokes shifts) from the light source (typically a laser) caused by energy loss due to the inelastic collisions between photons and molecules is what is detected. The advantage of this combination is the high similarity of the measurements which both rely on detection of radiation resulting from laser matter interaction so that the disclosed measurement system can use many of the same hardware components for both LIBS and Raman measurements. Moreover, besides the complimentary use of the hardware it was further demonstrated in U.S. Pat. No. 7,999,928 that subsequent PCA analysis of the combined spectral information lead to better classification than either of the techniques alone, leading to a reduction in the number of false positive determinations relative to either technique alone and an improved system for the identification (as opposed to the quantification) of target species in a sample.

IR absorption spectroscopy is another well known technique for determining compositional properties of a sample, such as identification and quantification of target species in say food and pharmaceuticals, or quality parameters, such as hardness of wheat, baking properties of flour or the quality of wine. Since IR absorption by species of interest in the sample matrix generally follows the Lambert Beer law (i.e. a linear relationship between absorption and amount of absorbing species) the detection of IR absorption more readily permits a quantitative determination of target species. In particular, IR absorption data in combination with sophisticated chemometric data handling can be used to provide this quantitative information regarding many types of sample matrix. The IR absorption technique is fundamentally different to Raman spectroscopy in that the latter relies on a polarizability of the molecule under study and the former on dipole moment changes during vibration. Consequently, species that are detectable by Raman are not usually readily detectable by IR absorption and vice versa. Moreover, Raman spectroscopy tends to be less sensitive than IR absorption spectroscopy and is therefore employed in the qualitative, rather than quantitative, determination of properties, such as presence of target species, of a sample.

One constraint on using IR, particularly near infrared ('NIR'), spectroscopy for the quantitative analysis of one or more target species is its sensitivity to matrix effects interfering with the weak molecular overtones probed in this wavelength range. To some extent such sensitivity can be compensated for using a large data set from a wide range of sample matrices which are chosen to encompass these variations combined with chemometric data analysis methods like PLS. For very complex matrices such an approach may, however, sometimes prove insufficient. This is the case when trying to use NIR for soil analysis where it has been concluded that only local calibrations of soil parameters on soils from similar parent material and climatic impacts can be realized ('Visible and Near Infrared Spectroscopy in Soil Science', B. Stenberg et. al., Advances in Agronomy', Vol. 107, 2010, Pages 163-215).

It is an aim of the present invention to mitigate at least one of the problems associated with the known IR absorption spectroscopy technique and provide a system and a method capable of permitting quantitative determinations of properties in a complex sample matrix, such as those related to target species or physical quality properties of, for example soil.

According to one aspect of the present invention there is provided a system for the determination of properties of a sample comprising a LIBS detector, having a laser for ablating a portion of the sample and an optical spectrophotometer for generating LIBS data representing a wavelength dependent intensity variation in optical energy emitted from the ablated portion; an infra-red absorption detector, having an infra-red energy source for illuminating at least a portion of the sample with infra-red energy and an optical spectrophotometer for generating illumination data representing a wavelength dependent intensity variation of infra-red energy after its illumination of the sample; at least one chemometric prediction model constructed to link features of both LIBS data and illumination data to a different specific property of the sample and executable by a data processor; and a data processor configured to receive the LIBS data and the illumination data; to construct a combined dataset derived from at least a portion of the LIBS data and at least a portion of the illumination data and to apply to the constructed data set the at least one chemometric prediction model to generate therefrom a determination of the specific property. It has been discovered that certain properties predicted using a combined dataset comprising both LIBS data and illumination data are predicted more accurately and have a better repeatability than the same properties predicted using either LIBS data or illumination data alone. The present invention therefore provides a system for determining properties of a sample having a better performance relative to a system which employs either of the individual techniques alone.

In one embodiment of the system according to the present invention at least one chemometric prediction model is constructed such that when applied in the data processor a quantitative determination of the property is generated.

In a further embodiment of the system there is provided a sample stage adapted for movement, preferably rotational movement, to effect a movement of a sample thereby exposing different portions for ablation by the laser and illumination by the infra-red energy and wherein the data processor is configured to receive LIBS data and illumination data from a plurality of portions as the sample is moved; to generate an average LIBS dataset and an average illumination dataset from the respective received LIBS and illumination data; and to apply the at least one prediction model to the combined dataset derived from data from both the average LIBS dataset and the average illumination dataset. By utilizing a dataset derived from LIBS and illumination data obtained from a plurality of different portions of the sample then any adverse effects on the data due to inhomogeneities of the sample may be mitigated and data that is more representative of the sample may be obtained.

According to a second aspect of the present invention there is provided a method of determining properties of a sample comprising the steps of: acquiring into a data processor LIBS data corresponding to wavelength dependent intensity variations of optical radiation having been emitted from at least a portion of the sample as a result of laser induced ablation of the portion; acquiring into the data processor illumination data corresponding to wavelength dependent intensity variations of illuminating infrared radiation after its interaction with at least a portion of the sample; in the data processor applying at least one chemometric prediction model, each constructed to link features of both LIBS data and illumination data to a specific property of the sample, to a combination of both the LIBS data the illumination data to generate therefrom a determination of the specific property linked by the prediction model.

These, as well as additional objects, features and advantages of the present invention, will be better understood through the following illustrative and non-limiting detailed description of embodiments of the present invention, made with reference to the drawings of the appended figures, of which:

Figure 1:
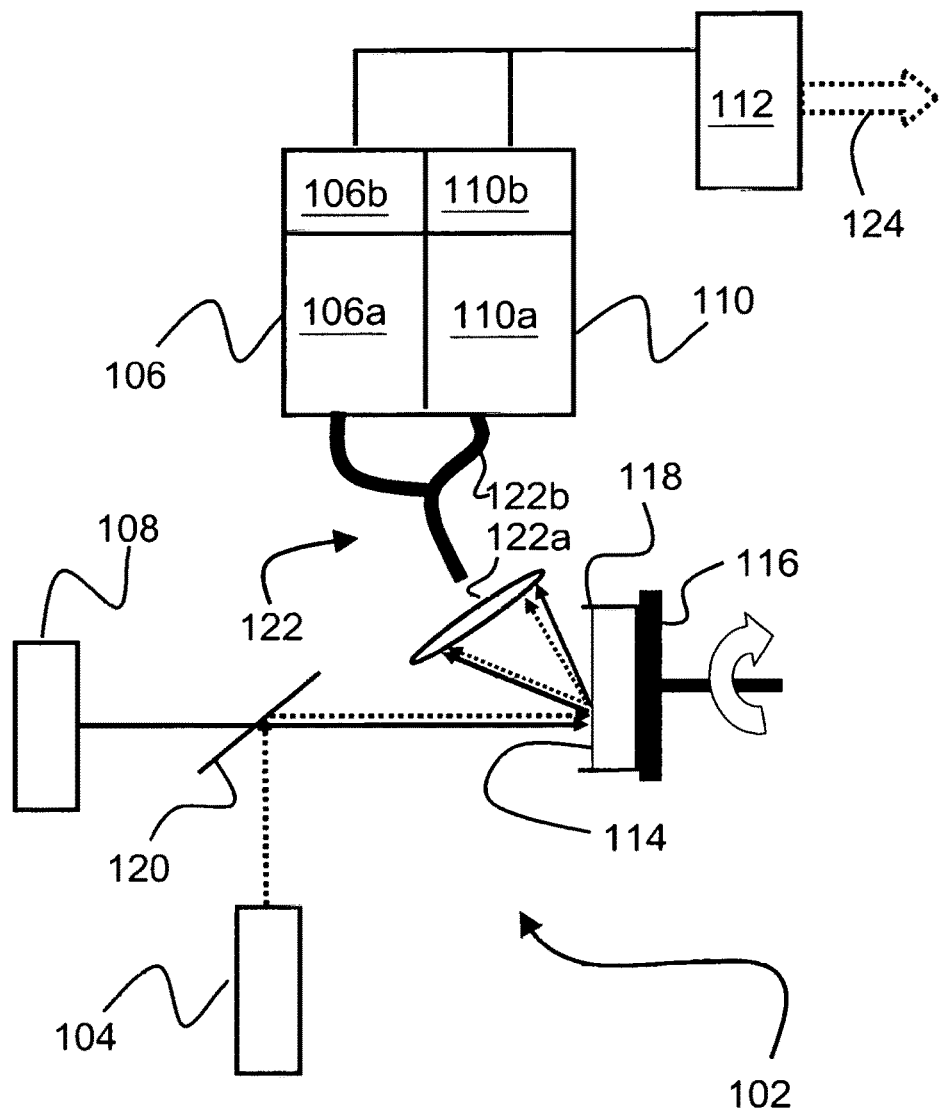
FIG. 1 shows a schematic block representation of an embodiment of a system according to the present invention.

A non-limiting exemplary embodiment of a system 102 according to the present invention is illustrated in FIG. 1. The system 102 comprises a LIBS detector, which includes a laser source 104 for ablating a region of the sample and an optical spectrophotometer 106; an infra-red absorption detector, which includes an infra-red (IR) energy source 108 for illuminating a region of the sample and an optical spectrophotometer 110; and a data processor 112 in operable connection with the outputs of both optical spectrophotometers 106,110. It will be appreciated from a consideration of the following that although the data processor 112 is illustrated as a single unit the present invention may also be realised using a data processor comprising physically separate elements for performing different functions ascribed to the single data processor 112 of the present embodiments and that these elements may be at locations remote from one another and, for example, interconnected via a telecommunications link.

The optical spectrophotometers 106,110 are in the present embodiment illustrated as being separate instruments but this is not essential and in other embodiments these may be combined into a single spectrophotometer instrument which utilises the same optical dispersion elements and/or detection arrangements. Each spectrophotometer 106, 110 (or alternatively the single spectrophotometer) is adapted to generate an output which represents a wavelength dependent intensity variation of input optical energy from a sample 114 for input to the data processor 112 (hereinafter referred to as 'LIBS data' when generated using the LIBS detector and as 'illumination data' when generated using the infra-red absorption detector). As will be appreciated the spectrophotometers 106,110 may be realised in a variety of known ways but, by way of example only, each spectrophotometer 106,110 of the present embodiment comprises a wavelength dispersion device 106a,110a having an output for optical energy to provide optical radiation at a detection device 106b,110b which converts optical intensity to a corresponding electrical signal for output to the data processor 112. It may be that the wavelength dispersion device 106a,110a of one or both spectrophotometers 106, 110 includes a movable dispersion element (such as a diffraction grating) which, as it is moved (most typically rotated) sweeps the wavelengths of incident optical radiation across an exit aperture and onto a single detection element of the detection device 106b, 110b. In an arrangement which is less sensitive to physical vibrations, the wavelength dispersion device 106a,110a of one or both spectrophotometers 106, 110 includes a static wavelength dispersion element which provides an optical output which is spatially dispersed by wavelength to an array of detection elements of the detection device 106b, 110b in which each element or perhaps sub group of elements of the array receives a separate and individually identifiable portion of the spatially separated wavelengths dispersed by the fixed dispersion elements of the dispersion devices 106a, 110a and converts these to individually identifiable electrical signals corresponding to the intensities of radiation at the separate elements or element sub groups.

Each of the laser source 104 and the IR energy source 108 is arranged to generate an output for incidence on a sample matrix 114 which may be prepared or unprepared and which is located at a sample stage 116, for example and not necessarily in a container 118. This arrangement of laser and IR energy outputs can be achieved in many ways, for example as illustrated for the present embodiment the laser source 104 and IR energy source 108 may be collocated to provide outputs which are orthogonal and intersect one another. An optic arrangement 120, here in the form of a semi-silvered mirror positioned at the intersection of the outputs and orientated at 45° to each, may be provided to direct the incident outputs towards the sample matrix 114. In another embodiment the optic arrangement 120 may be a fiber-optic arrangement for conveying the outputs to the sample matrix 114. In a further embodiment each of the laser source 104 and the IR energy source 108 may be arranged to direct their outputs to be incident at the sample matrix 114 without the need for an optical arrangement. However achieved it is preferable but not essential that the outputs from each of the laser 104 and IR energy source 108 are made incident upon substantially the same region of the sample matrix 114 to interact with substantially the same material of the sample matrix 114.

Collection optics 122 may be provided to collect radiation from the sample matrix 114 which results from an interaction between the incident outputs of the sources 104, 108 and the material of the sample matrix 114 and to provide this radiation for detection by one or both of the spectrophotometers 106,110, such as by the detection devices 106b, 110b. The collection optics 122 may be realised in a variety of ways and for example and without limitation the collection optics may comprise, as illustrated in the present embodiment, a pickup lens 122a which collects and focuses radiation from the sample matrix 114 onto an input of a fiber-optic 122b. The fiber-optic 122b conveys this radiation to the spectrophotometers 106,110 and which fiber-optic 122b, in the present embodiment, comprises a bifurcated output, one to each of the spectrophotometers 106,110.

In an exemplary mode of operation of a system according to the present invention, which will now be illustrated, by way of example only, with reference to the system 102 of FIG. 1, a sample matrix 114 is located at a measurement site within the system 102, at which site output from the laser 104 and the IR energy source 108 can each interact with the sample 114. The measurement site in the present embodiment is defined by a sample receiving stage 116 which may advantageously be movable, here rotatable to minimize size overheads, relative to the directions of travel of the outputs from the laser 104 and IR energy source 108. By effecting the relative movement of the sample matrix 114 the LIBS data and the illumination data may be obtained from different regions of the sample matrix 114 and the data from each region may be combined to provide an average data set for a larger region of the sample matrix 114 than those regions used to provide any one data set. The sample 114, in some cases may be placed in a sample retainer such as a sample cup 118 illustrated in FIG. 1 which itself is then placed on the sample receiving stage 116 (or more generally, at the measurement site). In other cases the sample may be placed un-retained on the sample receiving stage 116 (or more generally, at the measurement site). The sample 114 may also undergo some treatment prior to its interrogation using the LIBS 104,106 and the IR absorption 108,110 detectors, for example when the sample 114 is soil or other particulate material the sample material may be pressed so as to avoid voids in the sample.

After locating the sample 114 at the measurement site (sample receiving stage 116) each of the laser 104 and the IR energy source 108 is operated to illuminate a region, preferably the same region, of the sample 114. Operation of the sources 104,108 may be made simultaneously or sequentially. Simultaneous operation may give rise to the problem of radiation from one source creating an unwanted background signal for the detector incorporating the other source. Preferably but not essentially the two sources 104,106 are operated sequentially, most preferably the laser 104 is operated after the IR energy source 108 so that illumination data and LIBS data will originate substantially from the same material from the same region. This will provide a better correlation of data from the LIBS (104,106) and the infrared absorption (108,110) detectors since both data sets are then generated from substantially identical material. The IR energy source 108 is configured to generate IR energy which extends at least across the wavelength regions expected to be absorbed by the sample 114. The IR energy source 108 can be broadband or can be arranged to emit IR energy in a plurality of narrow, possibly overlapping or consecutive, wavelength bands. In operation of the system 102 the IR energy source 108 is energised and its IR energy output is made incident upon a region of the sample 114 which absorbs particular wavelengths dependent on the composition of the sample 114. This IR energy, after its interaction with the sample, is collected by the collection optics 122, passed to the infra-red absorption detector, in the present embodiment to the spectrophotometer 110 of the detector, and an output is generated corresponding to a wavelength dependent intensity variation of the interacted IR energy (optical absorption spectrum). This output is passed into the data processor 112 as illumination data, for example and by way of illustration only, representing intensity values measured at a plurality, m, of discrete wavelengths. Next, the IR energy source 108 is de-energised and the laser 104 is energised. The laser beam is made incident on the sample 114 and a portion thereof is ablated to form a plasma. Optical radiation which is generated as excited species in the plasma return to their lower energy state, emitting characteristic photons in the process, is collected by the collection optics 122, passed to the LIBS detector, in the present embodiment to the spectrophotometer 106 of the detector, and an output is generated corresponding to a wavelength dependent intensity variation (optical emission spectrum) of the plasma emissions and is passed into the data processor 112 as LIBS data, for example and by way of illustration only, representing intensity values measured at a same or different plurality, n, discrete wavelengths.

The data processor 112 is configured to combine the LIBS data and the illumination data into a single dataset ('combined dataset'). In the present embodiment and by way of a non-limiting example only, this combined dataset consists of m+n data points containing all the illumination and LIBS data points. The intensity values at each of these points may also undergo normalization or other data pre-treatment in the data processor 112.

A computer executable algorithm describing a multivariate chemometric prediction model which is constructed to link features of both LIBS data and illumination data to a property of the sample is made available to the data processor 112, for example from a computer memory or data storage device integral with and a component of the data processor 112 or from a remote storage device (not shown) which may in some embodiments be accessible to the data processor 112 via a telecommunications link. The data processor 112 is adapted to operate to apply the prediction model to the combined dataset to generate therefrom a determination of the property of the sample which is linked by the prediction model. One or more additional prediction models may be made accessible to the data processor 112, each model linking a different property to combined LIBS and illumination data, and the data processor adapted to apply one or more of these models to the combined dataset in order to obtain determinations of the properties linked by each corresponding prediction model. The results of each of such determinations may be provided by the data processor 112 as an output 124, for example as an output to a screen, printer or in other human discernible format or as an output in machine readable format.

Such prediction models are established using known chemometric techniques which employ either linear or non-linear multivariate statistical analysis, for example Partial Least Squares (PLS); Multiple Linear Regression (MLR); or Artificial Neural Network (ANN), to generate a mathematical relationship by which the combined dataset, derived from LIBS and illumination spectral data, may be quantitatively correlated with the properties of interest of the sample.

Figure 2:
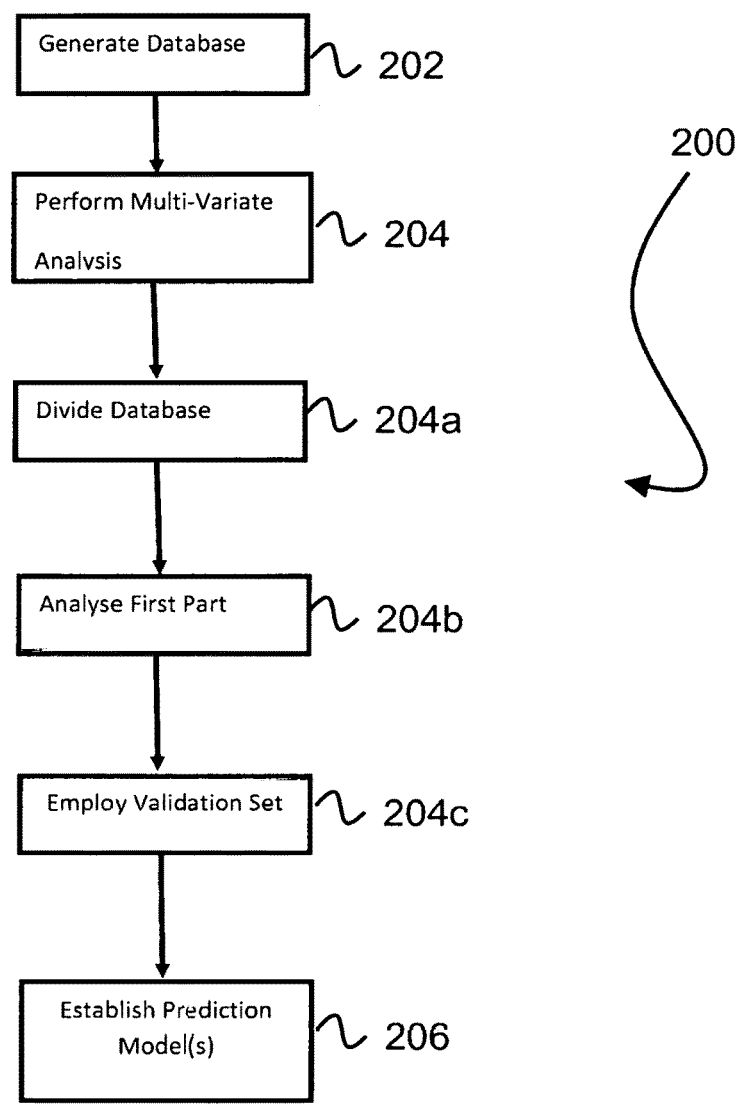
FIG. 2 shows a flow chart illustrating a method of establishing a prediction model that may be employed in the system of FIG. 1.

The chemometric prediction model which is employed in the data processor 112 may be constructed according to the flow chart illustrated in FIG. 2. A first step 202 in establishing such a prediction model is the generation of a database (or information matrix) wherein each record represents data from a calibration sample. In this database is stored LIBS data and illumination data from calibration samples (i.e. samples having the same matrix as samples the properties of which are to be predicted) indexed with other information obtained from the same calibration sample which identifies the presence and/or more usefully the amounts of a species the presence and/or amount of is to be determined in a test sample. This other information may be obtained using direct compositional analysis methods, such as say liquid or gas chromatography, on each of the calibration samples. Such other analysis methods, whilst they may provide a direct measurement of species of interest present in the sample matrix, are typically time consuming and expensive to perform.

At step 204 the contents of the database is subjected to a multivariate statistical analysis. In the present example this comprises the step 204a of dividing the database from step 202 into two parts. The first part is subjected to the multivariate analysis at step 204b. The second part is employed at step 204c as an independent validation set. It will be appreciated that the precise usage and division of the content of the database may vary.

At step 206 a prediction model is established by which is provided a mathematical relationship between input LIBS and illumination data in combination (the combined dataset) and a sample property a quantitative indication of which is to be predicted (general relationship: Property=Function {LIBS spectral data, illumination spectral data}). This model is for use in the data processor 112 for application to LIBS and illumination data combined to form a combined dataset for an unknown sample.

It will be appreciated that the prediction model according to the present invention may be established using additionally other data such as information regarding assessments of physical qualities of the calibration samples such as hardness or texture; information regarding temperature, physical location, sample pre-treatment conditions.

Example

Analysis of Soil

The combined information in the LIBS spectrum and NIR absorption spectrum is used for developing mathematical prediction models, each of which model is useful for the quantitative determination of a different property of soil samples. Soil samples were homogenised and pressed into tablets of about 40 mm in diameter and about 5 mm thickness using a simple hydraulic press. In the present example 5 tonnes was applied for 30 seconds and then 11 tonnes for a further 30 seconds to produce tablets in which substantially all air pockets are removed. Pressed tablets demonstrated much less fluctuations in their LIBS spectra as compared with uncompressed samples. Measurements were made on one hundred and six soil samples obtained from locations throughout North America. The resulting diversity of soil matrices and the limited number of samples used to generate a useful prediction model illustrates that present inventive combination of measurement modalities according to the present invention advantageously is able to compensate for complex matrices which neither measurement methodology alone can do. These samples were formed into tablets as described above and measurements obtained using a system generally as described in relation to that of FIG. 1 in order to generate LIBS and illumination datasets. The combined dataset, derived using data from both the LIBS and the illumination datasets, is used for generating one or more prediction models generally according to the process described in relation to FIG. 2.

Figure 4:
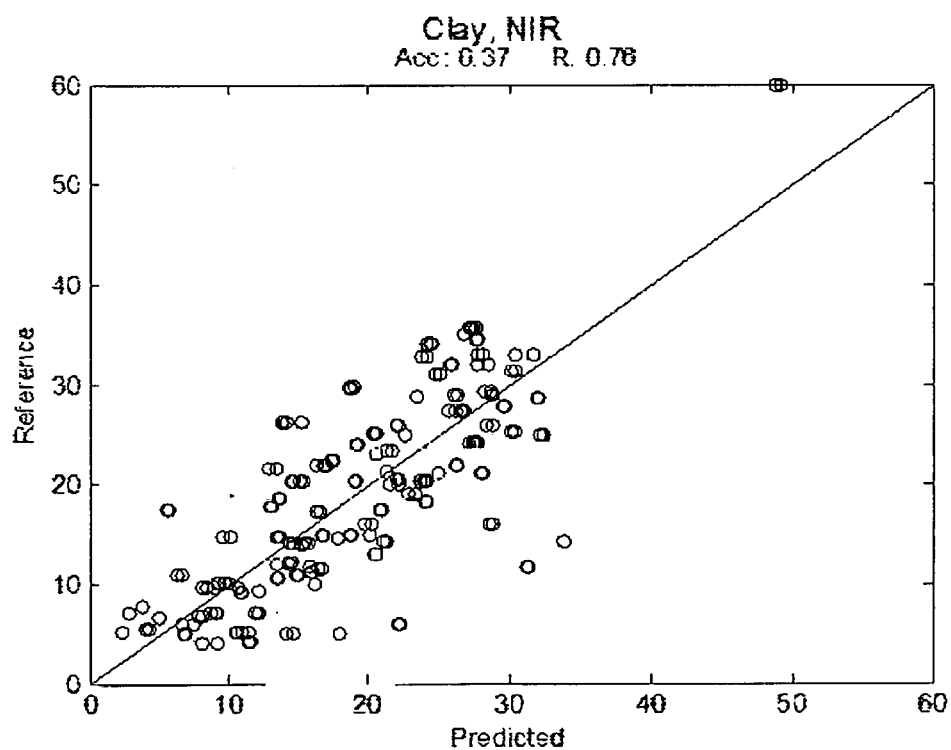
FIG. 4 shows a calibration curve for a prediction model for clay in soil established using only NIR absorption data.
Figure 5:
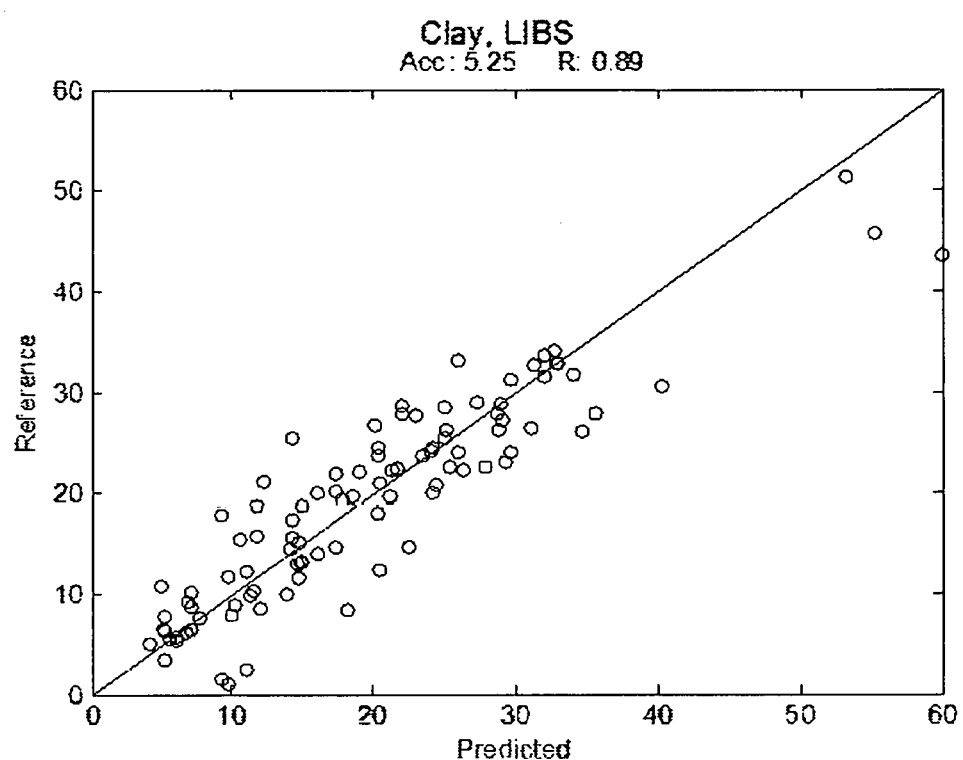
FIG. 5 shows a calibration curve for a prediction model for clay in soil established using only LIBS emission data.

In the specific example of clay content or 'texture' prediction (a quantitative prediction typically expressed in percent) some fifty calibration soil samples and 1 replicate were employed in order to establish the calibration and the remaining fifty six calibrations employed as the validation set. Each had its combined dataset (LIBS data+illumination data) indexed against clay content which was derived using the separation by sedimentation reference method. A PLS prediction model was constructed using the combined data set (FIG. 3) and compared against models constructed using only illumination data (here NIR absorption data) (FIG. 4) and LIBS data (FIG. 5).

Figure 3:
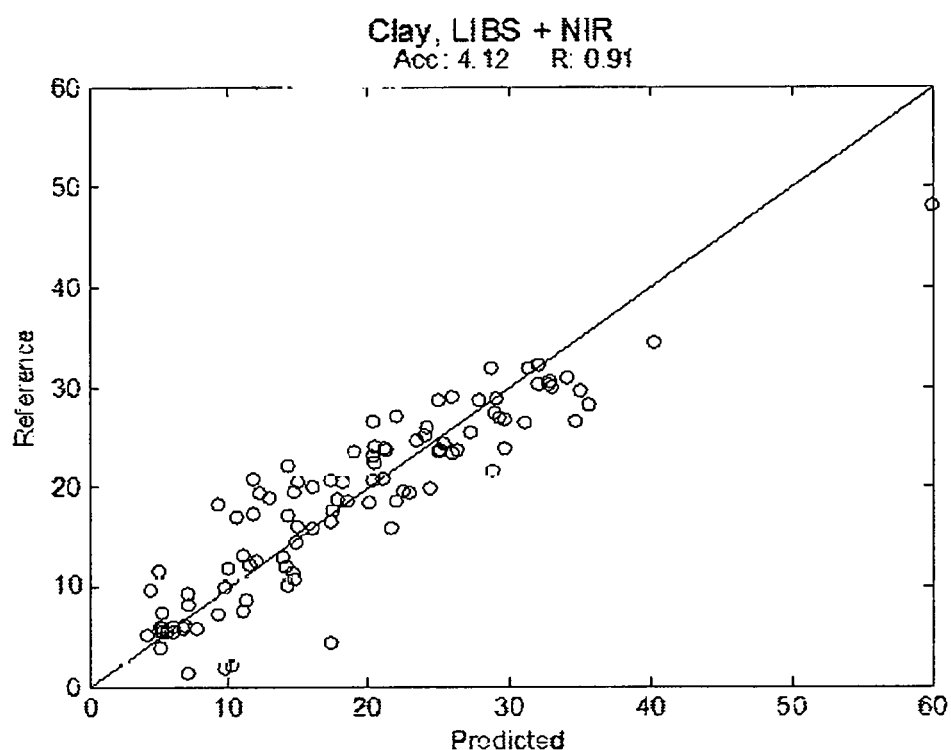
FIG. 3 shows a calibration curve for a prediction model for clay in soil established following the methodology illustrated in FIG. 2 and a combined dataset.

The PLS prediction model generated from the curve (straight line) illustrated in FIG. 3 employing the combined dataset provides a model having a prediction accuracy of 4.12 and a correlation of 0.91. As used here accuracy is defined as a measure of the standard deviation of the predicted values from the mean of the reference measurements (the reference method itself has an accuracy of 3.5 for clay) whilst correlation is a measure of the linear dependence between the plotted variables and ranges between −1 and +1 (+1 indicating strongest correlation). This may be compared to the PLS prediction model generated from the curve illustrated in FIG. 4 employing only the illumination (NIR absorption) dataset which model had a prediction accuracy of 6.37 and a correlation of 0.76. The PLS prediction model generated from the curve illustrated in FIG. 5 employing only the LIBS dataset is likewise worse than that generated using the combined dataset and has a prediction accuracy of 5.25 and a correlation of 0.89.

Total organic carbon (TOO) is another important parameter to quantify in soil as it characterises the humus content and hence the innate fertility of the soil. A second prediction model for TOO was also constructed (a quantitative prediction typically expressed in percent) in a manner described above in relation to the clay content prediction model. The reference method against which TOO was calibrated was the dry combustion method in which the amount $CO_2$ released for a heated soil sample is monitored. In the present example the same one hundred and six calibration soil samples were measured using the system generally described in relation to that of FIG. 1. Again the combined datasets from fifty samples were employed to establish a PLS prediction model and the combined datasets from the remaining fifty six were employed as the validation dataset.

Figure 6:
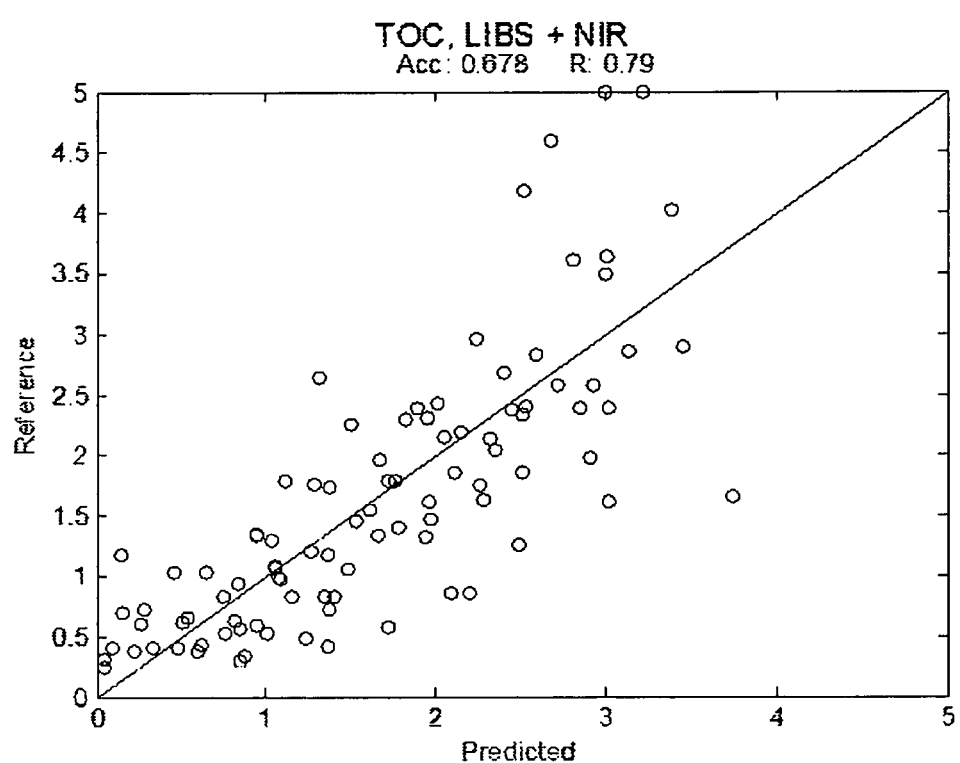
FIG. 6 shows a calibration curve for a prediction model for TOO in soil established using a combined data set and the methodology illustrated in FIG. 2.

The PLS prediction model generated from the curve illustrated in FIG. 6 employing the combined dataset has a prediction accuracy of 0.678 (as compared to the reference accuracy of 0.7) and a correlation of 0.79.

Other prediction models for properties of soil, such as cation exchange capacity or 'CEC' (a quantitative prediction typically expressed in $cmol_{(+)}/kg$), calcium or potassium contents (quantitative predictions typically expressed in parts per million 'ppm'), may be constructed in a similar fashion and some or all of them made available to the data processor 112 of FIG. 1 for application to combined datasets obtained for unknown soil samples using a system according to the present invention, such as that illustrated in FIG. 1.

Thus, by way of the present example, it has been illustrated that the system according to the present invention may be utilized to make quantitative measurements on even a highly complex sample matrix.

It will be appreciated that whilst the system and method according to the present invention has a particular application in soil analysis the present invention is not intended to be limited to use in this field. Indeed, the present invention may find uses in and bring its advantages to diverse fields such as explosive or other threat detection; food, drink and feedstuff monitoring or control; and biological fluid investigations. It will also be appreciated that the choice of analysis methodology is not limited to PLS but, as is known in the art of chemometrics, may be selected after a consideration of one or more of, for example, the linearity of the dataset, on the size and diversity of that dataset and whether a quantitative or a qualitative prediction is needed.

The invention claimed is:

1. A method, comprising:
controlling a laser induced breakdown spectroscopy (LIBS) detector to generate LIBS data based on laser induced ablation of at least a portion of a sample, the LIBS data corresponding to wavelength dependent intensity variations of optical radiation having been emitted from the portion of the sample;
controlling an infra-red absorption detector to generate illumination data based on illumination of at least the portion of the sample with infra-red energy, the illumination data corresponding to wavelength dependent intensity variations of illuminating infrared radiation reflected from the portion of the sample;
adjusting the sample to expose a plurality of portions of the sample to laser induced ablation and infra-red illumination;
constructing a combined dataset derived from at least a portion of the LIBS data and at least a portion of the illumination data; and
determining at least one property of the sample based on an association between the combined dataset and the at least one property of the sample.

2. A system for determining properties of a sample, the system comprising:
a laser induced breakdown spectroscopy (LIBS) detector, the LIBS detector including,
a laser configured to ablate a portion of the sample, and
an optical spectrophotometer configured to generate LIBS data, the LIBS data representing a wavelength dependent intensity variation in optical energy emitted from the ablated portion of the sample;
an infra-red absorption detector, the infra-red absorption detector including,
an infra-red energy source configured to illuminate at least a portion of the sample with infra-red energy, and
an optical spectrophotometer configured to generate illumination data, the illumination data representing a wavelength dependent intensity variation of infra-red energy reflected from the sample;
a sample stage configured to adjust the sample to expose a plurality of portions of the sample to ablation by the laser and illumination by the infra-red energy; and
a data processor configured to,
receive the LIBS data and the illumination data;
construct a combined dataset derived from at least a portion of the LIBS data and at least a portion of the illumination data; and
determine at least one property of the sample based on determining an association between the combined dataset and the at least one property of the sample.

3. The system as claimed in claim 2, wherein,
the optical spectrophotometer of the LIBS detector is configured to generate a plurality of instances of LIBS data based on laser induced ablation of the plurality of portions of the sample; and
the optical spectrophotometer of the infra-red energy source is configured to generate a plurality of instances of illumination data based on infra-red illumination of the plurality of portions of the sample.

4. The system as claimed in claim 3, wherein,
the data processor is configured to
generate average LIBS data based on an average of the plurality of instances of LIBS data,
generate average illumination data based on an average of the plurality of instances of illumination data, and
construct the combined dataset derived from at least a portion of the average LIBS data and at least a portion of the average illumination data.

5. The system as claimed in claim 2, further comprising:
collection optics configured to direct radiation emitted from the sample to each of the optical spectrophotometer of the LIBS detector and the optical spectrophotometer of the infra-red absorption detector.

6. The system as claimed in claim 5, wherein the collection optics includes,
a fiber-optic assembly and a pickup lens, the fiber-optic assembly including an input and at least one output, the at least one output configured to direct radiation to each of the optical spectrophotometer of the LIBS detector and the optical spectrophotometer of the infra-red absorption detector, and the pickup lens configured to focus the radiation emitted from the sample onto the input of the fiber-optic assembly.

7. The system as claimed in claim 6, wherein,
the fiber-optic assembly includes a bifurcated output configured to convey radiation to each of the optical spectrophotometer of the LIBS detector and the optical spectrophotometer of the infra-red absorption detector through separate outputs.

8. A system for determining properties of a sample, the system comprising:
a laser induced breakdown spectroscopy (LIBS) detection element, the LIBS detection element configured to generate LIBS data based on laser induced ablation of a portion of the sample, the LIBS data representing a wavelength dependent intensity variation in optical energy emitted from the ablated portion of the sample;

an infra-red absorption detection element, the infra-red absorption detection element configured to generate illumination data based on infra-red illumination of the sample, the illumination data representing a wavelength dependent intensity variation of infra-red energy reflected from the sample; and a sample stage configured to adjust the sample to expose a plurality of portions of the sample to ablation by a laser and infra-red illumination.

9. The system as claimed in claim 8, wherein, the LIBS detection element is configured to generate a plurality of instances of LIBS data based on laser induced ablation of the plurality of portions of the sample; and the infra-red absorption detection element is configured to generate a plurality of instances of illumination data based on infra-red illumination of the plurality of portions of the sample.

10. The system as claimed in claim 8, further comprising:

collection optics configured to direct radiation emitted from the sample to each of the LIBS detection element and the infra-red absorption detection element.

11. The system as claimed in claim 10, wherein the collection optics includes, a fiber-optic assembly including an input and at least one output, the fiber-optic assembly configured to convey radiation to each of the LIBS detection element and the infra-red absorption detection element; and a pickup lens configured to focus the radiation emitted from the sample onto the input of the fiber-optic assembly.

12. The system as claimed in claim 11, wherein, the fiber-optic assembly includes a bifurcated output configured to convey the focused radiation to each of the LIBS detection element and the infra-red absorption detection element through separate outputs.

* * * * *